United States Patent
Truex

(10) Patent No.: US 10,379,055 B2
(45) Date of Patent: Aug. 13, 2019

(54) GAS DETECTOR TUBE TEMPLATE AND METHODS OF READING GAS DETECTOR TUBES

(71) Applicant: NEXTTEQ LLC, Tampa, FL (US)

(72) Inventor: Bryan I. Truex, Tampa, FL (US)

(73) Assignee: Nextteq LLC, Tampa, FL (US)

( * ) Notice: Subject to any disclaimer, the term of this patent is extended or adjusted under 35 U.S.C. 154(b) by 420 days.

(21) Appl. No.: 15/062,891

(22) Filed: Mar. 7, 2016

(65) Prior Publication Data

US 2016/0258874 A1    Sep. 8, 2016

Related U.S. Application Data

(60) Provisional application No. 62/128,597, filed on Mar. 5, 2015.

(51) Int. Cl.
*G01N 21/78*      (2006.01)
*G01N 21/77*      (2006.01)
*G01N 21/29*      (2006.01)

(52) U.S. Cl.
CPC ......... *G01N 21/783* (2013.01); *G01N 21/293* (2013.01); *G01N 2021/7756* (2013.01)

(58) Field of Classification Search
CPC .................. G01N 1/00; G01N 21/783; G01N 2021/7756; G01N 21/293
See application file for complete search history.

(56) References Cited

U.S. PATENT DOCUMENTS

| 2,027,816 A | 1/1936 | Albert |
| 2,174,349 A | 9/1939 | Littlefield |
| 2,370,683 A | 3/1945 | Palma |
| 4,123,227 A | 10/1978 | Heim et al. |

(Continued)

FOREIGN PATENT DOCUMENTS

GB        2329017 A    10/1999

OTHER PUBLICATIONS

International Search Report and Written Opinion for corresponding International Application No. PCT/US16/21209 dated Jun. 3, 2016.

*Primary Examiner* — Dennis White
*Assistant Examiner* — Bryan Kilpatrick
(74) *Attorney, Agent, or Firm* — Pike IP Law, PLLC; Bernard G. Pike

(57) ABSTRACT

Gas detector tube templates are described. Gas detector tubes may be used to determine the concentration of target gases in a sampled gas either visually or electronically. Gas detector tubes for visual reading have the length-of-stain demarcations printed or etched on the transparent tube. However, the demarcations may interfere with electronic reading of gas detector tubes. Embodiments of a gas detector tube template may be used to accurately and reliably read gas detector tubes that do not have concentration demarcations printed on the tube in the working area adjacent to the chemical reagent. The gas detector tube template may have a gas detector tube holder capable of reversibly receiving a gas detector tube and two scale card holders. The gas detector tube template could have a left and right scale holder hingedly connected to the gas detector tube holder. The gas detector tube template may be used with scale cards capable of being, reversibly received in the scale rockets.

15 Claims, 4 Drawing Sheets

(56) References Cited

U.S. PATENT DOCUMENTS

| | | |
|---|---|---|
| 5,069,879 A | 12/1991 | Leichnitz et al. |
| 5,089,232 A | 2/1992 | May |
| 5,397,538 A | 3/1995 | Stark et al. |
| 5,415,838 A | 5/1995 | Rieger et al. |
| 5,464,588 A | 11/1995 | Baether et al. |
| 8,277,732 B1 | 10/2012 | Osborne et al. |
| 8,480,957 B2 | 7/2013 | Truex et al. |
| 2005/0250218 A1 | 11/2005 | Andrelczyk et al. |
| 2012/0063956 A1* | 3/2012 | Truex .................. G01N 21/783 422/86 |
| 2014/0051179 A1 | 2/2014 | Truex et al. |

* cited by examiner

GAS DETECTOR TUBE TEMPLATE AND METHODS OF READING GAS DETECTOR TUBES

RELATED APPLICATIONS

This application claims priority under 35 U.S.C. 119(a) to U.S. Provisional Patent Application No. 62/128,597 filed on Mar. 5, 2015 entitled "Gas Detector Tube Template and Method."

FIELD OF THE INVENTION

The invention relates to gas detector tubes, apparatuses, kits, and devices lot reading gas detector tubes, and methods of reading gas detector tubes. Embodiments of the apparatuses, kits, and devices are capable of being used to detecting and determining an approximate concentration of at least one target compound of a gas. Gas detector tubes comprise a transparent tube and a chemical reagent capable of changing colors when contacted by a target compound or class of target compounds. The apparatuses, systems and methods allow convenient reading, converting, and/or interpreting the colorimetric change of the chemical reagent to determine the concentration at the target compounds in the sampled gas.

After sampling of the environment by passing a gas through the gas detector tube, the resulting color change may be manually or electronically measured as a length-of-stain. The length-of-stain may be correlated to a concentration of a target gas by measuring the degree that a chemical reagent has undergone a color change by chemical reaction and the volume of sample drawn through the gas detector tube. In embodiments of the gas detector tube, the length-of-stain and/or color change may be determined visually with a scale card comprising demarcations associated with a detector tube without target gas concentration demarcations printed an the tube.

BACKGROUND OF THE INVENTION

There are a variety of apparatuses for measuring, the concentration of certain gaseous components of a gas mixture. Simple apparatuses, referred to as gas detector tubes, colorimetric tubes, or gas indication tubes ("gas detector tubes"), typically comprise a transparent tube and a chemical reagent within the transparent tube that is capable of reacting with a target chemical compounds resulting in a color change of the reagent. In a typical colorimetric gas detector tube, a known volume of air is passed through the tube with a pump or other device. The chemical reagent indicates the presence of target compounds by changing color from the inlet end of the tube. The resultant length-of-stain (the length of the color changed section of the chemical reagent) depend on the concentration of the target compounds in the gas which has passed through the tube in the known volume of gas. Colorimetric gas detector tubes are used throughout industry as a low-cost and easy-to-use tool for detecting the presence of target compounds in a sampled volume of gas. The tube is typically, made of glass or another transparent material so that the length-of-stain may be measured.

For example, conventional gas detector tubes comprise a glass tube filled with a chemical reagent that reacts to a specific target chemical compounds. The chemical reagent is sealed within the glass tube and retained in a defined position by gas permeable plugs in both ends of the glass tube. In some cases, the chemical reagent may be liquid impregnated into a porous chemically neutral solid substrate. Prior to use, the chemical reagent is protected from exposure to contaminants and chemical compounds by sealing the ends of the gas detector tubes into tips until use, thereby extending the shelf life of the gas detector tube prior to use. To use the gas detector tube, the tube on both ends of the detector tube are broken off to open a gas flow path through the tube and across the reagent. The air or other gas to be sampled may then be drawn through the tube and into contact the reagent with a fixed volume of a sample drawn through a volumetric sampling pump, for example. The reagent is capable of rapidly reacting with the target compounds as the sample is drawn through the tube. The amount of reaction and the degree of change of color of the reagent are related to the concentration of the target chemical compounds in the sampled gas, the amount of reagent in the tube, the flow area of the gas tube, and the volume of gas drawn through across the reagent. Since the sampled gas is drawn in one end of the gas detector tube and out the other end, the reagent begins to change color at the inlet end and the color change extends toward the outlet. The total length of the color change is commonly referred to as the "length-of-stain."

To determine the concentration of a target compound, a known volume of the sample gas may be drawn into the gas detector tube comprising a known quantity of reagent that reacts in a repeatable manner resulting in a color change with target compounds. After sampling the length-of-stain should correlate to the only unknown variable, the concentration of the gas. The length of the color change and the degree of color change of the reagent then corresponds to the concentration of the target compounds. Detector tubes that measure gas concentration by length-of-stain are reliable and simple to use after training.

To ensure more accuracy in measuring the concentrations of target gases, after manufacturing a batch of gas detector tubes, fixed volumes of gas with known concentrations of target compounds are passed through the gas detector tubes to develop a batch specific calibration curve relating the length-of-stain to corresponding gas concentration. The calibration curve is included with the detector tube to allow visual reading of the concentration of a gas in a sampled volume. From their first introduction the detector tubes have their scale printed separately, see, for example, U.S. Pat. No. 2,174,349 to J. B. Littlefield. As the leading edge of color change (closest to the exit end of the tube) of the reagent in the detector tubes is not always well defined, the scale divisions may be marked having a distance greater than length of diffusive front of discoloration. As such, the scales are of poor resolution and, more recently, the scales printed directly on the surface of the tube. For example, Dreager™, Gastec™, Kitagava™, Auer™, MSA™, RAY™, as well as other manufacturers of detector tubes have on their tubes the beginning of the scale first scale division, marked 3 to 5 mm from the end the first input plug. See FIG. 1. Because of possible channeling effects and other flow dynamics, resulting in different lengths visible on each side of the tube, the divisions are printed as rings around the tube and numbers representing concentrations are in close proximity or into broken portions of a ring. The drawback of the known art is that such detector tubes cannot be accurately and repeatedly read by an electronic device because of the concentration lines, concentration amounts, and other marks on the tubes obstructing optical reading of the length-of-stain. For example, the markings may be incorrectly interpreted by the device as a color change of the chemical reagent.

There has been a long felt need for a better more accurate and objective way of reading gas concentration with gas detector tubes. Heim et al, in U.S. Pat. No. 4,123,227 show a length-of-stain tube electronic reader based on detector tube without any printed matter. The detector tube serves as an alarming device and is periodically interrogated over a period of time. Leichnitz is at in U.S. Pat. No. 5,069,879 suggested tube having no scale on the readable part, of the surface and printed means introducing into electronic reader all specific data for the tube including calibration data. There is a significant drawback of the tunes manufactured to be read by electronic reader only; they may not also by read visually due to their lack of demarcations.

The contemporary art of colorimetric reading devices is developed in the direction of devices even more specifically designed for optic-electronic reader. U.S. Pat. No. 5,089,232 to May shows an arrangement of tube-like devices for only electronic reading. U.S. Pat. No. 5,197,538 to Stark et al., U.S. Pat. No. 5,415,838 to Rieger et al. and U.S. Pat. No. 5,464,588 to Bather at al. depict development of specific tube-like devices electronic reading of a zone of discoloration. Such devices, however, are highly specific and cannot be read without specialized electronic means.

Most color changes indicated by colorimetric reactions of the reagent depend to some extend on the ambient conditions such as temperature, relative humidity and barometric pressure.

There exists a need for an apparatus, kit, device, and method for visually or manually reading colorimetric detector tubes that do not include concentration demarcation marks.

SUMMARY

Gas detector tubes may be used to determine the concentration of target gases in a sampled gas. Traditionally, gas detector tubes have been read visually by comparing the length-of-stain of the reagent to a calibration curve printed or etched on the transparent tube. However, electronic tube readers that are capable of reading a length-of-stain by optical image technology and converting the length-of-stain to a concentration of target compounds by using a calibration curve stored in memory. Electronic tube readers are preferably used with gas detector tubes that comprise a transparent tube without concentration demarcations interfering with a clear view of the reagent.

Embodiments of a gas detector tube template may be used to accurately and reliably read gas detector tubes that do not have concentration demarcations printed on the tube in the area adjacent to the chemical reagent. In one embodiment, the gas detector tube template comprises a gas detector tube holder capable of reversibly receiving a gas detector tube and two scale card holders. The gas detector tube template may comprise a left scale holder hingedly connected to a left side of the gas detector tube holder, wherein the left scale holder comprises a left scale pocket and a right scale holder hingedly connected to at right side of the gas detector tube holder, wherein the right scale holder comprises a right scale pocket.

The gas detector tube template may be used with is scale cards capable of being reversibly received in the scale pockets, wherein the scale card comprises a first set of demarcations for interpreting a length-of-stain for a target compound in the gas detector tube on the one side, such as a front side, of the scale card. The scale card may further comprise a second set of demarcations for interpreting a length-of-stain for a target compound in the gas detector tube on a second side, such as a back side of the scale card. In some embodiments, the first set of demarcations is different than the second set of demarcations. For example, the first set of demarcations may be used for a first volume of gas passed through the gas detector tube for a specific target compounds and the second set of demarcations may be used for a second volume of gas passed through the gas detector tube for the specific target compounds. In another embodiment, the first set of demarcations may be for a first target compound and the second set of demarcations for a second target compound.

The gas detector tube template may further comprise a second scale card capable of being reversibly received in a second scale pocket, wherein the second scale card comprises the first set of demarcations on one side of the second scale card and the second set of demarcations on another side of the second scale card. As described above, the first set of demarcations may be used for a first volume of gas passed through the gas detector tube for a specific target compound and the second set of demarcations may be used for a second volume of gas passed through the gas detector tube for the specific target compounds.

As such, embodiments of the gas detector tube template and methods allow use of the gas detection by gas detector tubes either visually and with an electronic gas detector tube reader with optical imaging technology to allow a more accurate and flexible way of utilizing the gas detector tubes.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs, it will be further understood that terms, such as those defined commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

DESCRIPTION OF PREFERRED EMBODIMENTS OF THE INVENTION

Figure 1A:
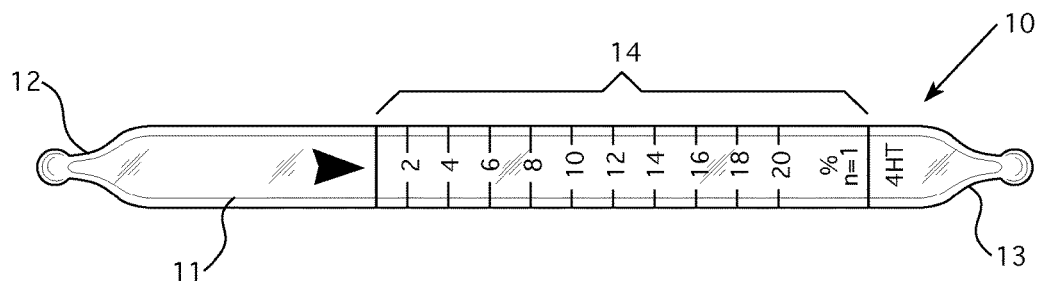
FIGS. 1A, 1B and 1C depict conventional gas detector tubes.

Gas detector tubes may be used to accurately and repeatedly determine the concentration of target gases in a sampled gas. Traditionally, gas detector tubes have been read visually by comparing the length-of-stain of the reagent exposed to its corresponding target compounds within the gas detector tube to a calibration curve printed on the transparent tube. However, electronic tube readers that are capable of reading a length-of-stain by optical image technology and convert the length-of-stain to a concentration of target compounds by using a calibration curve stored in memory are preferably used with gas detector tubes that comprise a transparent tube without concentration demarcations interfering with a complete view of the reagent.

As used herein, the term "transparent tube" means the tube of the gas detector tube has no demarcations or obstructions in the working area of the tube for viewing or electronically reading the length-of-stain of the chemical reagent.

As used herein, the term "working area" is the area used for viewing or electronic reading the length-of-stain between its minimum concentration reading and its maximum concentration reading through the readable range.

A gas detector tube template may be used to accurately and reliably read gas detector tubes that do not have concentration demarcations printed on the tube in the area adjacent to the chemical reagent. In one embodiment, the gas detector tube template comprises a gas detector tube holder capable of reversibly receiving a gas detector tube and two scale card holders. The gas detector tube template may comprise a left scale holder hingedly connected to a left side of the gas detector tube holder, wherein the left scale holder comprises a left scale pocket and a right scale holder hingedly connected to a right side of the gas detector tube holder, wherein the right scale holder comprises a right scale pocket.

Gas detector tubes are typically manufactured with a specific chemical reagent to determine the concentration of at least one target gas, family of target gases comprising a similar functional group, or class of target gases (collectively "target gas") in a sample gas. Typical chemical reagents for gas detector tubes comprise porous solid particles with pathways between the particles that allow as to flow through the porous solid from an inlet of the gas detector tube to an outlet of the gas detector tube or the chemical reagent is on the surface of a porous solid substrate. The chemical reagent will change color when the reagent is in contact with the chemical reagent ("colorimetric reaction"), typically the chemical reagent and the target gases will react resulting in the color change. As a sample passes through the gas detector tube, the target gases are involved in the colorimetric reaction with the chemical reagent until the target gases are depleted from the sampled gas. Many reagents for use in gas detector tubes are known and applicable to embodiments of the gas detector tubes. A sample is typically drawn through the gas detector tubes by a sampling pump. Common sample pumps include handheld piston pumps or bellows pump that are capable of accurately and repeatedly drawing a known volume of air.

Typically, the chemical reagent is fixed in place within the tube by two porous solid plugs at either end of the reagent within the tube. As the sample gas comprising target gases is drawn through an inlet of the gas detector tube, the chemical reagent near the inlet will begin to change color and if the concentration of the target gases is with the readable concentration range of the gas detector tube, the chemical reagent near the exit of the tube will remain unchanged. The length of the color change of the reagent ("length-of-stain") within the tube will correspond to the total amount of the target gases that were passed through the gas detector tube. It a known volume of gas is passed through the tube, a concentration of the target gases may be determined. Conventional gas detector tubes have a scale printed on the glass tube over the chemical reagent that may be used to approximate the concentration of the target gases for a known volume of the sampled gas. Each gas detector tube will have a readable concentration range for the target gases, if the gas concentration range is exceeded for a volume of sample, the chemical reagent will change color throughout its entire length and a concentration of the target gas may not be conventionally determined or if the concentration of the target gas is too low, the chemical reagent may not record a sufficient color change to determine the concentration of target gases. In such cases, a different tube with the appropriate concentration range may be used or the volume of sampled gas may be increased or decreased to produce a reading within the scale. For some gas detector pump and gas detector tube systems, up to a five-fold increase in sampled volume is recommended. The scale of the gas detector tube must then be adjusted to account for the different sample volume and the demarcations as printed on the gas detector tube do not accurately indicate the concentration of the target gas in the sample.

Gas detector tubes may be read either electronically by an electronic as detector tube reader or visually by a user by a simple comparison of the length-of-stain with one or more scales inserted into a gas detector tube template. Embodiments of the gas detector tubes may be read either visually or by an electronic gas detector tube reader without any obstruction of the reagent by demarcations or other markings in the working area of the gas detector tube. Further, embodiments include gas detector tubes comprising a tube surface that does not comprise marking, demarcations, or shading that obstructs the view of a portion of the reagent required for reading the length-of-stain after drawing a sample through the tube. Any number of scales may be used with the gas detector tubes. For example in one embodiment, each gas detector tube may comprise 2 to 5 different scales for visual reading of the gas concentration based upon the volume of sample drawn through the detector tube and the concentration of the target compound(s) in the sample. For example, the gas detector tube shown in FIG. 1A is designed for use with three different concentration ranges of the target concentration.

Figure 1B:
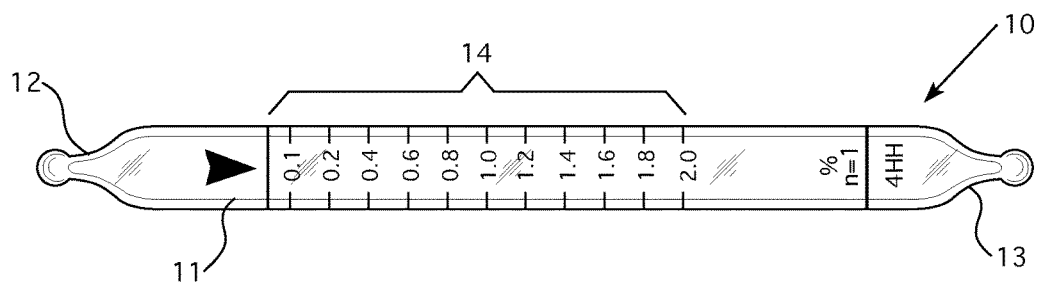
Figure 1C:
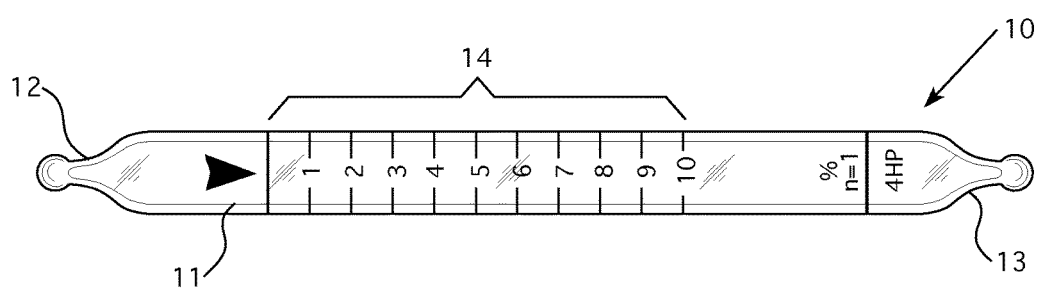

The gas detector tubes 10 of FIGS. 1A, 1B and 1C comprise a transparent tube 11. During storage and prior to use, the transparent tube is a sealed with a tip 12 at the inlet end and a tip 13 at the outlet end. As used herein, "tube" means a conduit defining a flow path of any cross-sectional shape. The cross-sectional shape may no circular, oval, rectangular, square, rectangular, polygonal, or any desired cross-sectional shape. The tube may be sealed simply by heating and pinching the ends of the tubes to seal for tips, using caps, septums or other means to seal the tube as understood by one skilled in the art.

Embodiments of the gas detector tubes may comprise a transparent tube 11 made from a glass or transparent plastics such as, but not limited to, acrylic, polycarbonates, copolymers of polyethylene and polypropylene, polyesters as well as other transparent materials. The gas detector tubes may also comprise demarcations 14 corresponding to the percentage of a target compound in a sample drawn through the gas detector tube based upon the acquired length-of-stain and the volume of the sample drawn through the gas detector tube. As previously stated, additional compensation factors may be used.

For example, for one pump stroke of a standard gas detector tube pump (100 milliliters), the gas detector tube of FIG. 1A may properly indicate a concentration between 2% and 20% of the target compound(s) in the 100 milliliter sample drawn through the tube.

If one pump stroke (n=1) does not produce a length-of-stain indicating that the concentration of the target compound(s) is greater than 2%, an additional pump stroke (totaling two pump strokes, n=2) of 100 milliliters may be drawn through the gas detector tube of FIG. 1A. However, since the demarcations printed on the glass of the gas detector tube are to be used with one pump stroke, the concentration amounts need to be divided by two to indicate the actual concentration of the target compound(s) in the 200 milliliter sample. Thus, the gas detector tube may properly indicate a concentration between 1% and 0% of the target compound(s) in the 200 milliliter sample drawn through the tube.

Further, if one pump stroke (n=1) produces a length-of-stain indicating that the concentration of the target compound(s) is greater than 20%, the reading cannot be properly interpreted and the gas detector tube must be discarded. A new similar gas detector tube may be used with a half pump stroke (n=½) of 50 milliliters may be drawn through the new gas detector tube of FIG. 1A. However, since the demarcations printed on the glass of the gas detector tube are too be used with one 100 milliliter pump stroke (n=1), the concentration amounts need to be multiplied by two to indicate the actual concentration of the target compound(s) in the 50 milliliter sample. Thus, the gas detector tube may properly indicate a concentration between 20% and 40% of the target compound(s) in the 50 milliliter sample drawn through the tube.

To improve optico-electronically reading of gas detector tubes, gas detector tubes without any demarcations printed on the transparent portion over the chemical reagent in the working area is recommended. Therefore, some gas detector tubes, preferably, do not have a scale printed, etched or otherwise applied to it. The same detector tubes that are to be read manually are the same detector tubes that can be used in an electronic tube reader ensuring lower inventory stocking levels plus ensuring greater assurance that the inventory will not be obsolete. The same inventory of unmarked glass detector tubes can be used in the tube reader or can be read manually with the gas detector tube template and the two printed scales (front and back) on the at least two scale cards that are provided with each box of detector tubes. In addition, additional scale cards could be provided for the same tube increasing, the number of applications that can be measured with a single tube part number.

Gas detector tubes without scale demarcations cannot be directly read visually without a separate scale. However, visual reading of gas detector tubes is complicated by the variety of scales and/or calculations required for different volumes of sample (numbers of pump strokes) drawn through the gas detector tubes. The operator must remember to count the number of strokes then read the tube markings to determine the factor needed to properly calculate the concentration reading from the gas detector tube scale demarcations.

A gas detector tube template may be used in conjunction with an electronic tube reader to reliably read the length-of-stain in the gas detector tubes. The gas detector tube template may be provided with each electronic detector tube reader assembly to verify readings of the electronic tube reader or to read gas detector tube manually if a problem is encountered with the electronic tube reader. In one embodiment, the gas detector tube template will be tethered or strapped to the tube reader body or the scale reader template is stored in the electronic tube reader assembly such at it is available with the electronic tube reader.

Embodiments of a gas detector tube template comprise a gas detector tube holder capable of reversibly receiving a gas detector tube and at least two wings or scale holders connected to the gas detector tube housing. Each wing or scale holder comprises a pocket for reversibly receiving at least one scale card for interpreting a length-of-stain in the gas detector tube. The scale holders may comprise transparent portions on both sides so that demarcations on both sides of the scale card may be viewed through the transparent portions to interpret the length-of-stain in the gas detector tube.

One or more sets of scale cards could be designed for use with each gas detector tube. Embodiments of a gas detector tube kit would comprise a gas detector tube including a specific chemical reagent and several scale card included in each box of gas detector tubes such that the value of the discoloration layer of an activated detector tube could be read with an electronic tube reader without demarcations or the detector tube may be read manually in the event the tube reader had dead batteries or had some other problem by using the gas detector to template with the appropriate scale cards.

An example of two scale cards with scales printed on both sides is shown below. A first scale card has a front side A and a back side B and a second corresponding scale card for insertion in a second wing has a front side C and a back side D.

TABLE 1

| A<br>Front Side | B<br>Back Side | C<br>Front Side | D<br>Back Side |
|---|---|---|---|
| 10 ppm | 5 ppm | 10 ppm | 5 ppm |
| 5 ppm | 1 ppm | 5 ppm | 1 ppm |
| 2 ppm | 500 ppb | 2 ppm | 500 ppb |
| 0 ppm | 250 ppb | 0 ppm | 250 ppb |
| 500 ppb | 125 ppb | 500 ppb | 125 ppb |
| First scale card front and back | | Second scale card front and back | |

The first and second scale card may both be inserted with the front sides facing forward or the scale cards may be positioned in the pockets with a front side facing forward and a rear side facing forward. For example, the A and C side could be used together in the wings of the tube reader. Each set has two identical scales on the two front sides and a different identical scale on the pieces of paper for the two back sides.

Figure 4:
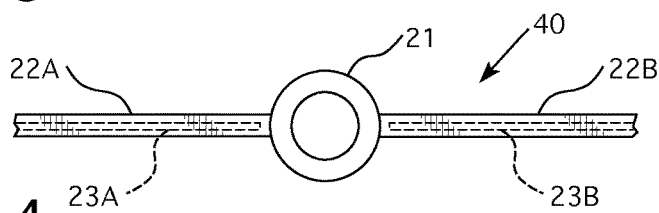
FIGS. 4, 5 and 6 depict different embodiments of the gas detector tube template comprising gas detector tube holders having various shapes.
Figure 5:
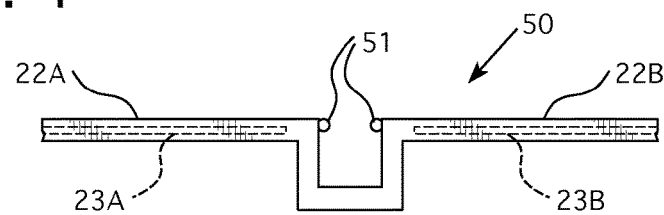
Figure 6:
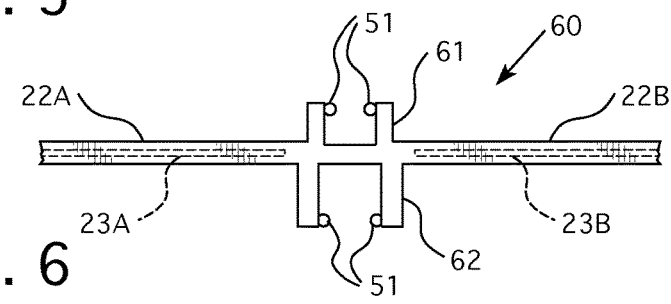
Figure 7B:
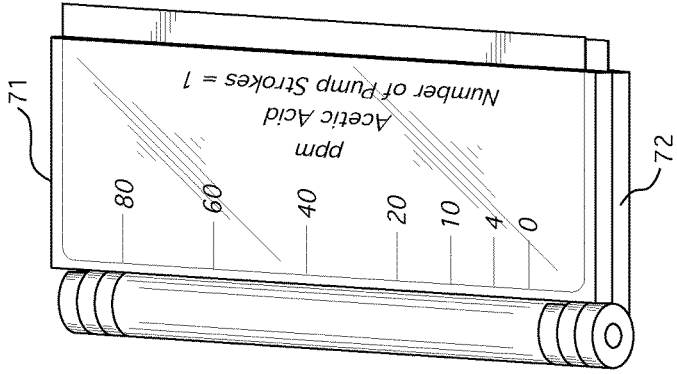
FIG. 7B depicts the embodiment of the gas detector tube template of FIG. 7 folded.

The gas detector tube holder may be any shape capable of securely holding a gas detector tube so that the length-of-stain by may be interpreted. For example, the holder may be cylindrical (See FIG. 4), partial cylindrical, rectangular channel (See FIG. 5 and FIG. 6), oval, a combination of these shapes, or other appropriate shape. The tube holder may further comprise a retainer assembly or a stop to hold the gas detector tube in a properly aligned position with the demarcations on the scales. A retainer assembly of the gas detector tube template 40 comprises at least two retainer protrusions 51 to hold the gas detector tube in position. The retainer protrusions may be made of natural or synthetic rubber, plastic, or other resilient material, for example. The retainer assembly may further comprise a retainer that may be an arm that may be swiveled over the tube after placing the tube in the holder or may be retaining loops (See FIG. 3, for example) or straps. The gas detector tube holder may further comprise a stop 33 for properly positioning the gas detector tube in the holder 21. The stop 33 may be adjustable to assist in aligning the gas detector tube with the demarcations on the scales. (See FIG. 7C)

Figure 2:
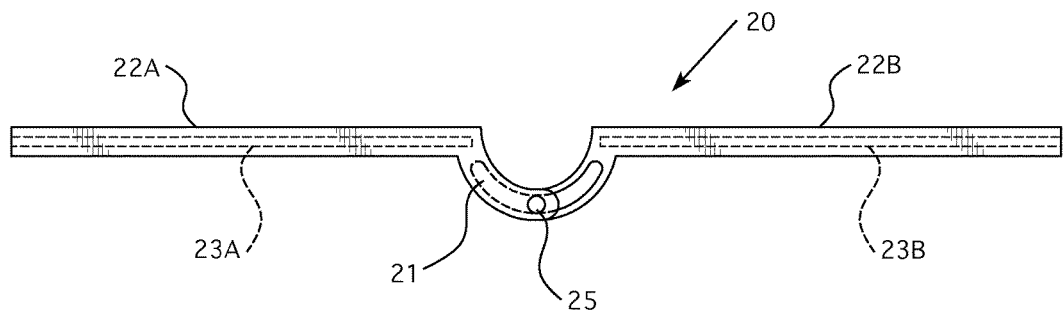
FIG. 2 depicts a gas detector tube template comprising a gas detector tube holder, a left wing and a right wing with pockets for removably receiving scale cards, wherein the wings are hinged to rotate relative to the gas detector tube holder.

An example of the gas detector tube template 20 is shown FIG. 2. The gas detector tube template 20 comprises a gas detector tube holder 21 having a shape of a partial cylinder. Typically, gas detector tubes have an outside diameter of 5 mm or 7 mm. Therefore, the inside radius R of the gas detector tube holder 21 is sized to fit either one or both sizes of gas detector tubes. The gas detector tube template 20 also comprises a left wing or scale holder 22A and a right wing or scale holder 22B connected to the gas detector tube holder 21. Each wing comprises a pocket (a left scale pocket 23A and a right scale pocket 23B) capable of reversibly receiving a card demarcations corresponding to the percentage of a target compound in a sample drawn through the as detector tube based upon the acquired length-of-stain, in the embodiment shown in the FIGS. 1, 2, 2A, 7A and 7B, the pocket is located on an edge of the scale holders. The scale card may be made of paper, card board, or plastic, for example. The two scale cards may have different scales printed on the front side and the back side. The scale cards may be sized to fit securely within the scale card pockets but when properly inserted still extend out of the pocket to allow the scale card to be grasped for removal. In such embodiments, the scale cards have a greater face surface area than the scale card pockets.

The two scale cards may have one detector tube scale printed on one side and a different scale printed on the other side of the scale card. In one embodiment, the gas detector tube template will have a raised portion that will fit with a cutout in the scale card in order to help properly align the scale card with the template and/or detector tube.

In some embodiments, the gas detector tube holder has a hinge in the center allowing the wings of the scale holder to lay horizontal or to be raised at an angle to the detector tube being read with the scales in the wings of the scale holder template. The rotation of the scale card wings around the circumference of the gas detector tube allows more accurate reading of the target gas concentration because the length-of-stain may be different at different places in the chemical reagent due to channeling or other reasons. For example, embodiments of the gas detector tube template 20 may further comprise a hinge connection 25 incorporated into the gas detector tube holder 21. The hinge connection allows the scale holder or wing to be rotated along the circumference of the gas detector tube to better read the length-of-stain at various points in and around the tube. In many cases, the length-of-stain does not have a discrete end point and the leading edge of the length-of-stain may be ragged, pointed or channeled. Rotating the scale around the circumference of the gas detector tube allows more accurate reading of the gas detector tube. In addition, the wings 22A 22B may be rotated such that the opposite face of a scale card inserted into the pocket 23B, for example is shown on the upper surface. In certain embodiments, the hinge allows the template to slide apart to make space for the detector tube to be cradled between the two wings. The hinge may be a mechanical hinge or a hinge made of a resilient material such as a plastic or rubber.

Figure 2A:
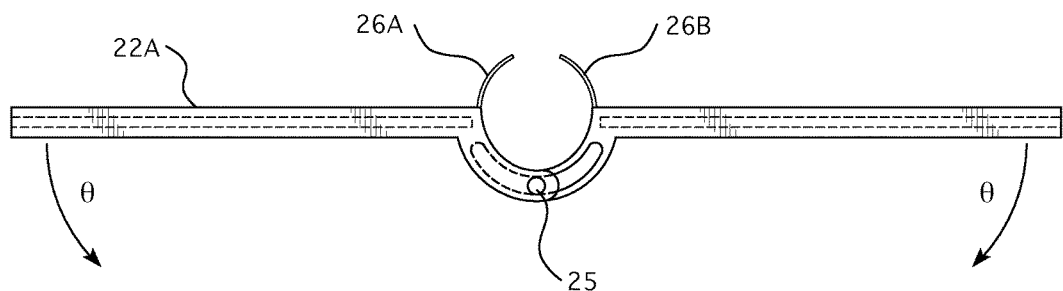
FIG. 2A depicts gas detector tube template comprising a gas detector tube holder with gas detector tube retainers and a left wing and a right wing with pockets for removably receiving scale cards, wherein the wings are hinged to rotate relative to the gas detector tube holder.

Embodiments of the gas detector tube template 20 may also comprise hinge 25 such that the wings 22A 23A may be rotated in the direction θ shown in FIG. 2A. A right holder tine 26A is separated from the right holder tine 26B to open the gas detector tube holder 21 to allow a gas detector tube to be placed in the gas detector tube holder 21. As the hinged is reverted to the original position (shown in FIG. 2A), the tines 26A and 26B retain the gas detector tube in the gas detector tube holder 21.

Figure 3:
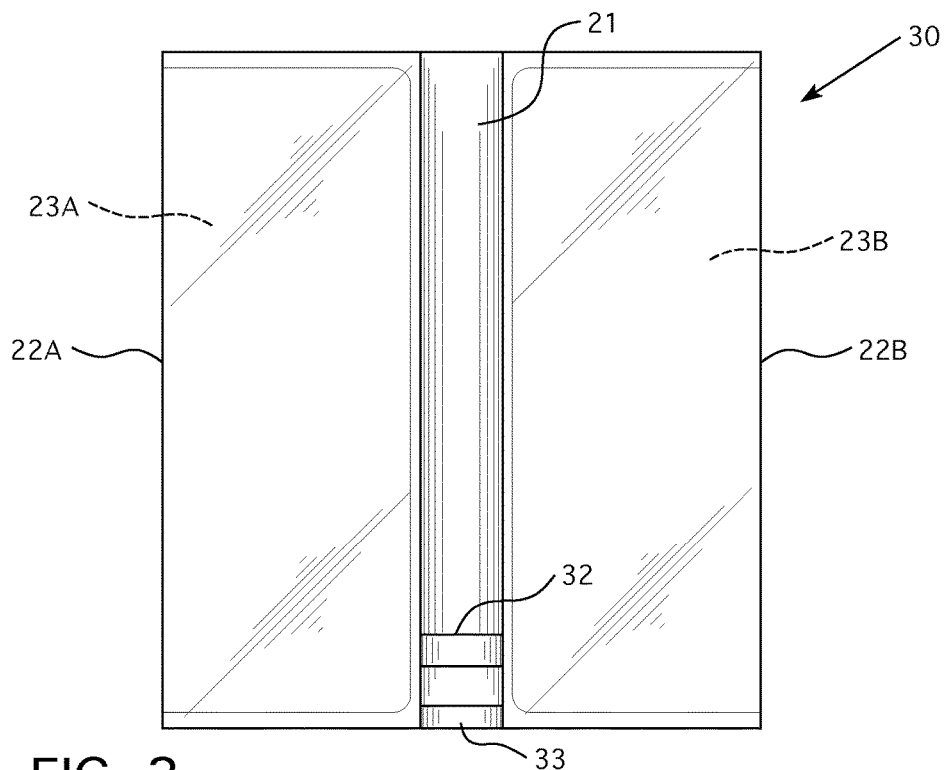
FIG. 3 depicts a top view of a gas detector tube template comprising a different embodiment of a gas detector tube retainer and scale pockets on a top surface of the scale holders.

FIG. 3 depicts an embodiment of the gas detector tube template comprising wings with pockets 23A 23B recessed in the top surface of the wings. The scale card has a complementary shape as the pocket so that the scale card may fit the pocket securely and be removed without damage. The left wing 22A and right wing 22B are transparent so that the underside (the side in contact with the bottom of the pocket) may be seen through the wing.

In another embodiment, the gas detector tube template may comprise a first detector tube holder 61 and second detector tube holder 62 connected to the two scale holders. The first gas detector tube holder 61 may be sized for one size gas detector tube such as a 5 mm diameter gas detector tube) and the second gas detector tube holder 62 may be sized for a different size gas detector tube (such as a 7 mm diameter gas detector tube).

Figure 7:
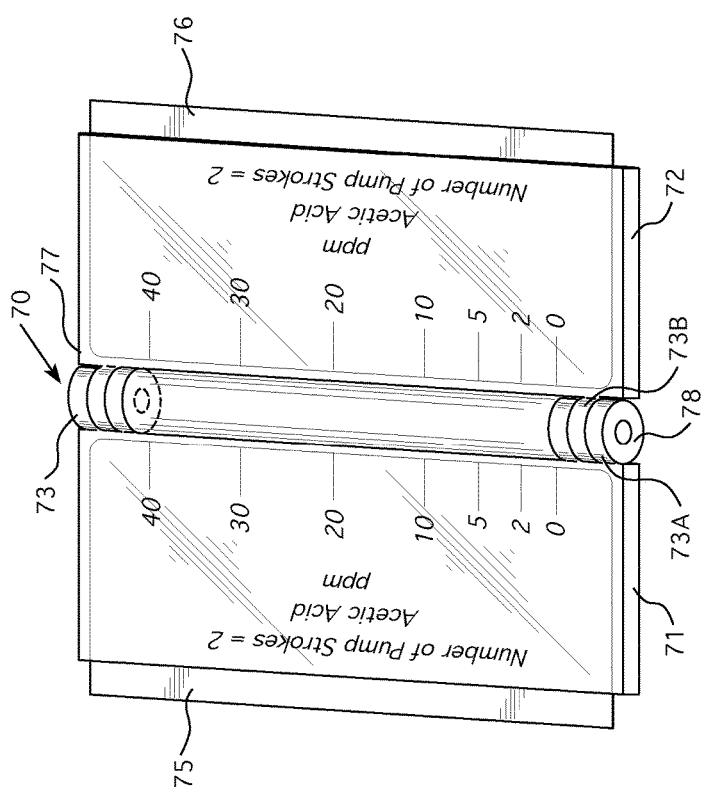
FIG. 7 depicts a gas detector tube template comprising a gas detector tube holder, a left wing and a right wing with scale cards removably inserted in the scale pockets, wherein the wings are binged to rotate relative to the gas detector tube holder.
Figure 7C:
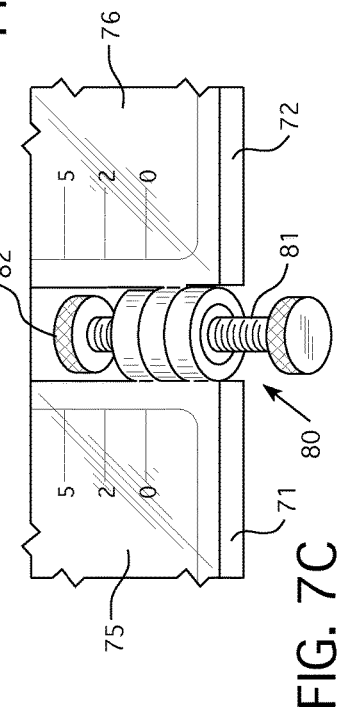
FIG. 7C depicts a gas detector tube template comprising a gas detector tube alignment assembly.

An embodiment of a gas detector tube template 70 is shown in FIG. 7. The gas detector tube template 70 comprises a left scale holder 71 and a right scale holder 72 that are hingedly connected by hinge 73. The hinge 73 allows relative rotation of the left wing 71 and right wing 72. In some embodiments of the gas detector tube template 70, the hinge 73 comprises detents on the knuckle 73A of the one wing 71 that interact with the recesses on knuckle 73B of the other wing 72. The detents interact with the recesses to fix the hinge in various positions to assist in reading the length-of-stain at various angular positions.

The embodiment of a gas detector tube template 70 is shown in FIG. 7 is shown with a left scale card 75 inserted into the pocket of the left wing 71 and a right scale card 76 inserted into the pocket on the edge of the right wing 72. The scale cards comprise different, scales on the front and back. In the example shown, an operator expected a concentration of acetic acid between 2 ppm and 40 ppm. The operator inserted the appropriate scale cards for this application that require two pump strokes (n=2). However, after the first pump stroke the length-of-stain extended into the readable scale because the concentration of acetic acid was higher than expected. Because the gas detector tube template 70 comprises wings that are hingedly connected and the scale card comprise one scale on the front side (showing concentration demarcations corresponding to the concentration of the target gas after two pump strokes) and a different scale on the back side (showing concentration demarcations corresponding to the concentration of the target gas after one pump stroke), either wing may be rotated on the hinge to reveal the back side scale to interpret the length-of-stain as shown in FIG. 7B wherein left wing 71 was rotated on top of right wing 72 to reveal the back side of scale card 75. As such the scale cards have different demarcations on each side, wherein the different demarcations correspond to different volumes of the sample drawn through the gas detector tube. The scale wings may be rotated around the gas detector tube without rotation of the tube. In some embodiments, the gas detector tube remains stationary and the wings rotate around the stationary tube. In such cases, the scale cards may comprise the same scale on both sides of the card such that as the wing is rotated around gas detector tube, the same scale may be used to read the channeling of the gas resulting front channeling, for example.

The gas detector tube template 70 further comprises a gas detector tube holder situated between the top portion 77 of the hinge 73 and the bottom portion of the hinge 78. In an embodiment shown in FIG. 7C, the hinge of the gas detector tube template is shown with an alignment mechanism 80 for moving a gas detector tube axially in relation to the gas detector tube holder to align the bottom of the chemical reagent with the zero concentration demarcation on the scale card. The alignment mechanism comprises a threaded rod 81 that extends through a threaded bore through the pin that extends through knuckles of the hinge. The threaded rod may be rotated to adjust the base 82 that the gas detector tube rests on for reading. Since the gas detector tube tips are broken prior to use, the length of the used gas detector tubes may be different and must be properly aligned in the template to determine the correct length of stand and therefore the concentration of gas present in the sample. In one embodiment of the gas detector tube template, wherein the scale holder comprises alignment marks to align the detector tube with the scale card.

An embodiment, of a method of interpreting a length-of-stain on a gas detector tube comprises down loading a scale card from the internet. The gas detector tube, gas detector tube packaging or instructions may include a code for accessing, downloading, and/or printing a correct scale card for a certain application. There may be several scale cards associated with each gas detector tube. The cards may comprise different scale demarcations based upon the volume of the sample drawn through the gas detector tube, for example.

An embodiment of the method would include the two scales being retained and accessible on a website in the following format and with the following information:

TABLE 2

| Tube Part No. | Lot No. | First Scale | Second Scale | Instruction Sheet |
| --- | --- | --- | --- | --- |

The scale cards could them be printed for each type of tube and for each specific lot of that type of tube. This retention on the website of key scale information would allow continuous access to the relevant information concerning the detector tube part number, lot number and the correct scales to use with the specified part number and lot number; thus allowing a user to properly read the detector tubes.

EXAMPLE

Determining the Concentration of Hydrogen Sulfide

In some cases, determining the concentration of one target compound may have as many as eleven (11) separate detector tubes with 11 different $H_2S$ concentration scales printed on the eleven different detector tubes. For example, GASTEC CORPORATION™ produces eleven tubes for determining the concentration of hydrogen sulfide ($H_2S$) in a sampled gas. The 11 different detector tubes and scales are based upon just three different detector tube reagent compound formulations for detecting hydrogen sulfide and detector tube scales for each of the three reagent formulations as follows:

TABLE 3

| GASTEC ™ Detector Tube Part Number | Reagent Formulation Type | No. of Scales and P/N |
| --- | --- | --- |
| 4HT, 4HP, 4HH | A = $H_2S$ + $CUSO_4$ → CUS + $H_2SO_4$ | 3 |
| 4H, 4HM, 4M, 4L, 4LL, 4LK | B = $H_2S$ + $Pb(CH_3COO)2$ → PbS + $2CH_3COOH$ | 6 |
| 4LB, 4LT | C = $H_2S$ + $HgCl_2$ − HCL | 2 |
| | Total Number of Tube Part Numbers and Scales | 11 |

Each of GASTEC™'s eleven $H_2S$ detector tubes have three ranges for each scale except for Tube 4HH that only has two ranges. There are a total of 32 ranges for $H_2S$ measurements with eleven scales defined by GASTEC™'s eleven detector tube part numbers. However, there are only three discrete detector tube reagent formulations housed in three different detector tubes and each of the detector tubes is identical in length. Using an electronic tube reader and applying the desired scale and ranges electronically to each of the three reagent formulas tubes shows that one detector tube for each chemical reagent formulation could replace all 11 different $H_2S$ tubes with printed scales. This is accomplished electronically by identifying the reagent formula and then telling the tube reader the electronic scale and ranges to use for each detector tube reading for each detector tube based upon the applicable reagent formula.

In the same way new scales could be created to center the desired concentration in the middle of the detector tube for greater accuracy. In addition, specialized scales could be created with electronic scales to suit customer's specific needs that would be too expensive to create with scales printed on the tubes because of the limited demand. Finally, because of the greater resolution possible with an electronic scale as opposed to a scale printed on the detector tube, scales that would not be possible to print on the detector tube because of physical limitations are now possible using an electronic scale of the tube reader.

The use of an electronic reader would allow for the production of much larger generic production of detector tubes based upon the detector tunes reagent formulation, thus lowering costs and reducing inventory carrying costs of 11 different detector tubes with different scales that could be replaced by producing just three detector tubes. This analysis of only manufacturing three tubes for 11 part numbers is true provided that the different part numbers associated with the different $H_2S$ tube reagent formulas also (i) specify the identical filtering media to limit or protect against different cross interferences and (ii) the interior diameter of the detector tubes is identical. If different filtering media is used with different part numbers using the same reagent formulas or if the different part numbers define detector tubes with different interior radiuses, then the 11 $H_2S$ tubes will not be able to be produced from three tubes.

For the $H_2S$ detector tube reagent formulations, the following is the number of ranges for each scale as follows:

Three Reagent Formulations $A=H_2S+CUSO_4 \rightarrow CUS+H_2SO_4$ $B=H_2S+Pb(CH_3COO)2 \rightarrow PbS+2CH_3COOH$ $C=H_2S+HgCl_2 \rightarrow HgCL+Base \rightarrow Chlorine$ (or $HgSHCl+HCl$)

TABLE 4

| | Reagent Formulation | Scales | P/N | Ranges |
|---|---|---|---|---|
| 1 | A = | 2-20% | 4HT | 3 |
| 2 | A = | 1-10% | 4HP | 3 |
| 3 | A = | 0.1-2.0% | 4HH | 2 |
| | Subtotal | 3 | | 8 |
| 4 | B | 1-2000 ppm | 4H | 3 |
| 5 | B | 50-800 ppm | 4HM | 3 |
| 6 | B | 25-250 ppm | 4M | 3 |
| 7 | B | 10-120 ppm | 4L | 3 |
| 8 | B | 5-60 ppm | 4LL | 3 |
| 9 | B | 2-20 ppm | 4LK | 3 |
| | Subtotal | 6 | | 18 |
| 10 | C | 1-6 ppm | 4LB | 3 |
| 11 | C | 0.2-2.0 ppm | 4LT | 3 |
| | Subtotal | 2 | | 6 |
| | Total $H_2S$ | 11 | | 32 |

The embodiments of the described gas detector tubes, gas detector tube readers and methods are not limited to the particular embodiments, components, method steps, and materials disclosed herein as such components, process steps, and materials may vary. Moreover, the terminology employed herein is used for the purpose of describing exemplary embodiments only and the terminology is not intended to be limiting since the scope of the various embodiments of the present invention will be limited only by the appended claims and equivalents thereof.

Therefore, while embodiments of the invention are described with reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

The invention claimed is:

1. A gas detector tube template, comprising:
    a gas detector tube holder capable of reversibly receiving a gas detector tube; and
    a left scale holder hingedly connected to a left side of the gas detector tube holder, wherein the left scale holder comprises a left scale pocket;
    a right scale holder hingedly connected to a right side of the gas detector tube holder, wherein the right scale holder comprises a right scale pocket;
    a right scale card capable of being reversibly received in the right scale pocket, wherein the right scale card comprises a first set of demarcations for interpreting a length-of-stain for a target compound in the gas detector tube on the front side of the right scale card and a second set of demarcations for interpreting a length-of-stain for a target compound in the gas detector tube on the back side of the right scale card, wherein the first set of demarcations is different than the second set of demarcations; and
    a left scale card capable of being reversibly received in left scale pocket, wherein the left scale card comprises the first set of demarcations front side of the left scale card and the second set of demarcations on the back side of the left scale card.

2. The gas detector tube template of claim 1, wherein the gas detector tube holder is cylindrical, partial cylindrical, oval shaped.

3. The gas detector tube template of claim 1, comprising a second detector tube holder hingedly connected to the left scale holder and the right scale holder.

4. The gas detector tube template of claim 1, wherein the gas detector tube does not have set of demarcations for interpreting a length-of-stain for a target compound printed on gas detector tube.

5. The gas detector tube template of claim 1, wherein the two scale holders comprise at least one transparent portion to view the demarcations on the front side and the back side of the scale cards.

6. The gas detector tube template of claim 1, wherein the scale pockets are located on a top surface of the scale holders.

7. The gas detector tube template of claim 1, wherein the scale pockets are located on an edge of the scale holders.

8. The gas detector tube template of claim wherein the demarcations correspond to the percentage of a target compound in a sample drawn through the gas detector tube.

9. The gas detector tube template of claim 1, wherein the different demarcations correspond to different volumes of the sample drawn through the gas detector tube.

10. The gas detector tube template of claim 1, wherein the scale cards were printed from an online source based upon the target compound and volume of sample drawn through the gas detector tube.

11. The gas detector tube template of claim 1, wherein each of the scale holder comprise an alignment mark to align the detector tube with the scale cards in the scale holders.

12. The gas detector tube template of claim 1, comprising a retainer assembly capable of securely retaining the gas detector tube in the gas detector tube holder.

13. A kit for interpreting gas detector tubes, comprising:
    a gas detector tube comprising a reagent, wherein the reagent changes color with exposure to a target compound and the gas detector tube does not have demarcations corresponding to the percentage of the target compound in a sample drawn through the gas detector tube based upon the acquired length-of-stain;

two first scale cards, wherein each first card comprises demarcations on both a front side and a back side, wherein the demarcations correspond to the percentage of a target compound in a sample drawn through the gas detector tube based upon, an acquired length-of-stain and the demarcations on the front side of the scale card is different from the demarcations on the back side of the scale card; and the gas detector tube temple of claim 1 comprising a holder for removably receiving the gas detector tube and two pockets to reversibly receiving the two scale cards, and alignment indicia for aligning the scale cards for properly reading the percentage of the target compound in the sample.

14. The kit for interpreting gas detector tubes of claim 13, further comprising two additional scale cards, wherein each additional scale cards comprises demarcations corresponding to the percentage of a second target compound in a sample drawn through the gas detector tube based upon an acquired length-of-stain and the demarcations on the additional scale cards is different from the demarcations on the first scale cards.

15. The kit for interpreting gas detector tubes of claim 13, further comprising an electronic gas detector tube reader.

* * * * *